(12) United States Patent
Tang et al.

(10) Patent No.: US 9,919,995 B2
(45) Date of Patent: Mar. 20, 2018

(54) PHOTOACTIVATABLE CAGED COMPOUNDS WITH AIE CHARACTERISTICS: METHOD OF PREPARATION AND APPLICATIONS

(71) Applicant: Benzhong Tang, Hong Kong (HK)

(72) Inventors: Benzhong Tang, Hong Kong (HK); Yee Yung Yu, Hong Kong (HK); Tsz Kin Kwok, Hong Kong (HK); Ju Mei, Hong Kong (HK)

(73) Assignee: Benzhong Tang (CN)

( * ) Notice: Subject to any disclaimer, the term of this patent is extended or adjusted under 35 U.S.C. 154(b) by 0 days.

(21) Appl. No.: 14/752,481

(22) Filed: Jun. 26, 2015

(65) Prior Publication Data

US 2015/0376112 A1 Dec. 31, 2015

Related U.S. Application Data

(60) Provisional application No. 61/998,413, filed on Jun. 27, 2014.

(51) Int. Cl.
*C07C 205/34* (2006.01)
*C07C 37/02* (2006.01)
*C07C 201/12* (2006.01)
*C09B 11/00* (2006.01)

(52) U.S. Cl.
CPC ............ *C07C 205/34* (2013.01); *C09B 11/00* (2013.01)

(58) Field of Classification Search
CPC .............................. C09B 11/00; C07C 205/34
See application file for complete search history.

(56) References Cited

U.S. PATENT DOCUMENTS

| | | | |
|---|---|---|---|
| 5,635,608 A * | 6/1997 | Haugland | A61K 41/0042 536/1.11 |
| 7,304,168 B2 | 12/2007 | Li et al. | |
| 8,153,103 B2 | 4/2012 | Li et al. | |
| 8,617,827 B2 | 12/2013 | Hell et al. | |
| 2006/0240565 A1* | 10/2006 | Tang | G01N 21/6428 436/164 |
| 2007/0074967 A1* | 4/2007 | Nagano | C07D 311/82 204/157.81 |
| 2008/0220407 A1* | 9/2008 | Tang | G01N 21/6428 435/4 |
| 2013/0059392 A1* | 3/2013 | Tang | G01N 21/643 436/80 |

FOREIGN PATENT DOCUMENTS

WO 1998/006875 A1 2/1998

OTHER PUBLICATIONS

Yu et al. ("A tetraphenylethene-based caged compound: synthesis, properties and applications", Chemical Communications (Cambridge, United Kingdom), (Jun. 2, 2014), 50, pp. 8134-8136).*
Yu et al. ("A tetraphenylethene-based caged compound: synthesis, properties and applications", Chemical Communications (Cambridge, United Kingdom), (published online Jun. 2, 2014), bibliographic data, 2 pages.*

* cited by examiner

*Primary Examiner* — Rosalynd A Keys
(74) *Attorney, Agent, or Firm* — Novick, Kim & Lee, PLLC; Allen Xue

(57) ABSTRACT

A photoactivatable caged compound (TPE-C) with AIE characteristics is designed and synthesized. TPE-C is non-emissive either in solution or in aggregated state, but its luminescence can be induced to emit strong cyan emission in aggregated state by UV irradiation. Such property enables TPE-C to be applied in photo-patterning and anti-counterfeiting related areas.

11 Claims, 12 Drawing Sheets

PHOTOACTIVATABLE CAGED COMPOUNDS WITH AIE CHARACTERISTICS: METHOD OF PREPARATION AND APPLICATIONS

FIELD OF THE INVENTION

The present invention relates to the synthesis and applications of caged compounds with AIE characteristics, in which the luminescence of the caged compounds could be photoactivated by lights in aggregated and solid states.

BACKGROUND OF THE INVENTION

Caged luminophores, whose luminscence is partially or completely quenched by a quencher but can be recovered upon cleavage of the quencher under certain stimulus such as UV or thermal treatment, are a type of typical photoactivatable materials and have been well studied and applied in many technological fields especially those related to biological applications such as macromolecular movement tracking and super-resolution imaging. For macro-molecules tracking, caged compunds can highlight a partistic area or organelle to monitor and study. For super-resolution imaging, caged luminophores can be turned on and off to record signals which accumulate to produce the super-resolution imaging. 2-Nitrobenzyl group is the most representative quencher for caged luminophores. Because of strong electron-withdrawing ability of 2-nitrobenzyl group, the emission of luminophore in the caged compound is quenched through photo-induced electron transfer (PET) process. These concepts have already demonstrated by traditional fluorophores such as BODIPY, fluorescein and rhodamine. However, those conventional fluorophores are suffered from aggregation-caused quenching (ACQ) effect, in which their emission is weaken or quenched when the molecules are aggregated in a condensed phase. Such ACQ effect in conventional fluorophores has greatly limited to utilize them in solid state or biological applications.

Inventions of caged luminophores have been reported in prior art, examples of which have been reported by Stefan W. Hell (U.S. Pat. No. 8,617,827 B2), Wen-Hong Li (U.S. Pat. No. 7,304,168 B2, U.S. Pat. No. 8,153,103 B2) and Joan C Politz (WO1998006875 A1).

SUMMARY OF THE INVENTION

In this invention, we introduce a concept on designing and synthesizing caged luminophores with AIE characteristics and exploring their applications. Herein, we reported a newly designed caged compound (TPE-C), which constructed by an AIE-active tetraphenylethene (TPE) derivative as a luminophore with a 2-nitrobenzene group as a quencher. TPE-C is non-fluorescence either in solution or in aggregated state but its emission in aggregated state can be photoactivated upon UV irradiation and consequently a strong cyan emission can be observed. Such property of the caged fluorophore enables it to be applied in photo-patterning and anti-counterfeiting related applications. As an object of the present invention, there is provided a group of novel caged compound, which constructed by an AIE derivative as a luminophore with a 2-nitrobenzene group as a quencher.

In the present invention, the caged compound is 2-nitrobenyl-functionalized AIE derivatives which can be photoactivated by lights.

In the present invention, the AIE derivatives are selected from active tetraphenylethene (TPE) derivates.

In the present invention, the caged compound comprises a formula selected from the group consisting of:

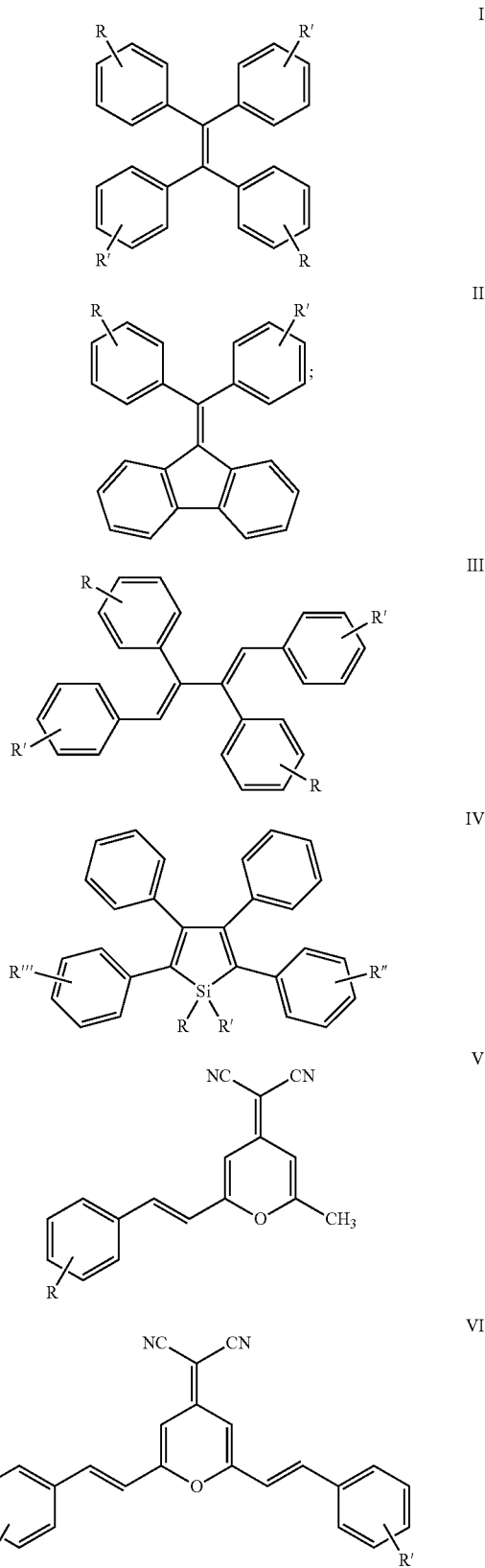

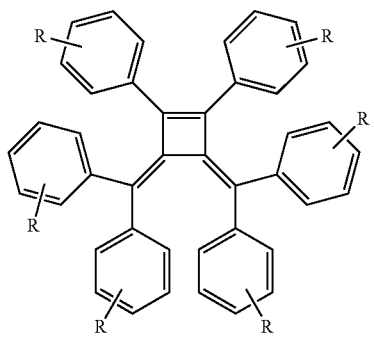
VII
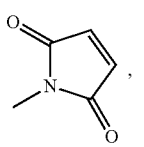, 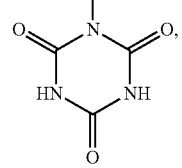
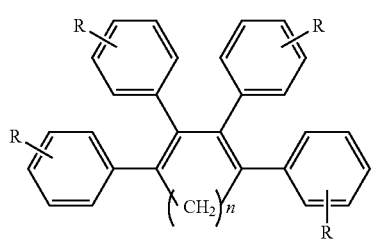
VIII
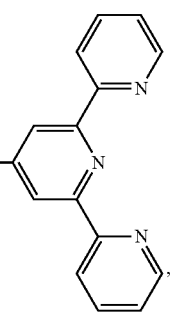, 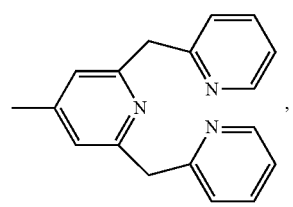
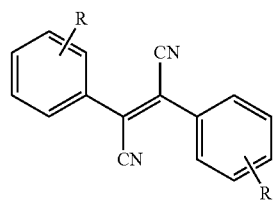
IX
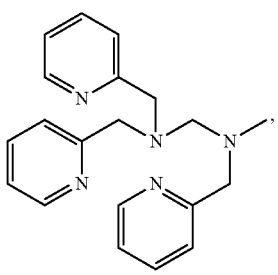
wherein at least one of R, R', R'' or R''' is
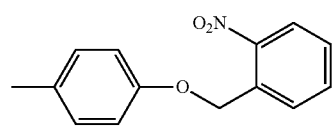 [SMILES: Cc1ccc(OCc2ccccc2[N+](=O)[O-])cc1]
R, R', R'' or R''' are independently selected from H,
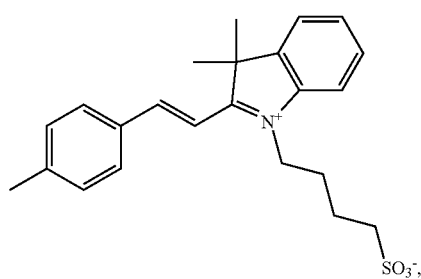
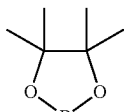
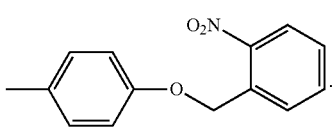.
In the present invention, the caged compound is selected from the following compound TPE-C.

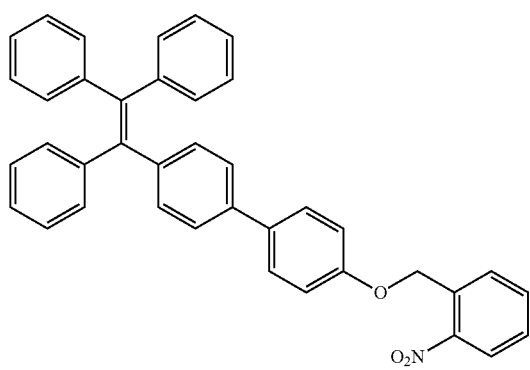
TPE-C
The present invention is directed to a process for preparing the above caged compound, wherein the process comprises a reaction between a formula I' to formula IX' and
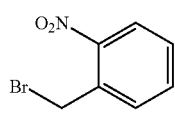
(compound 3)
(preferably, in the presence of $Cs_2CO_3$),
wherein the formula I' to formula IX' is selected from the group consisting of:
I'
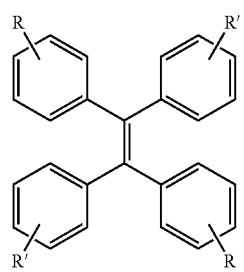
II'
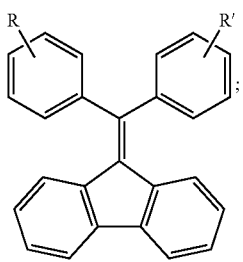
III'
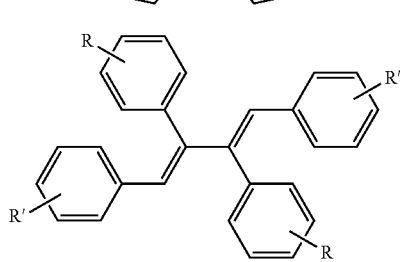
IV'
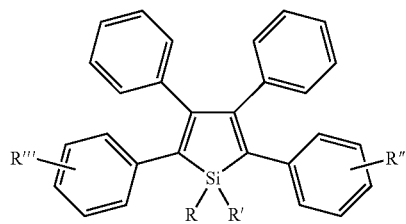
V'
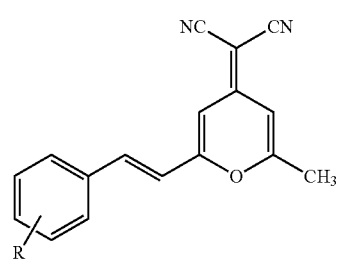
VI'
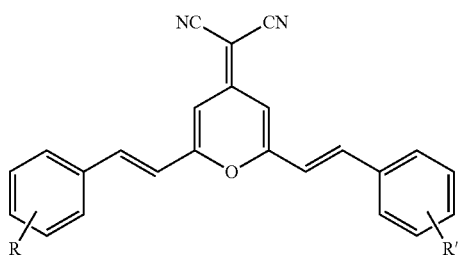
VII'
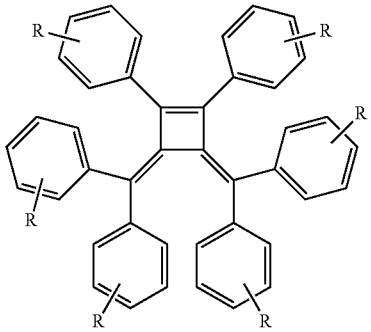
VIII'
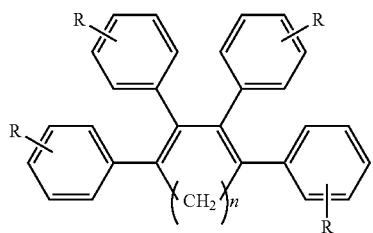
IX'
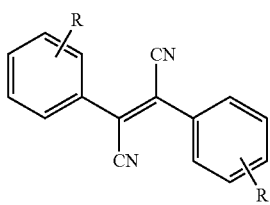

wherein
R, R', R" or R'" are independently selected from: H,

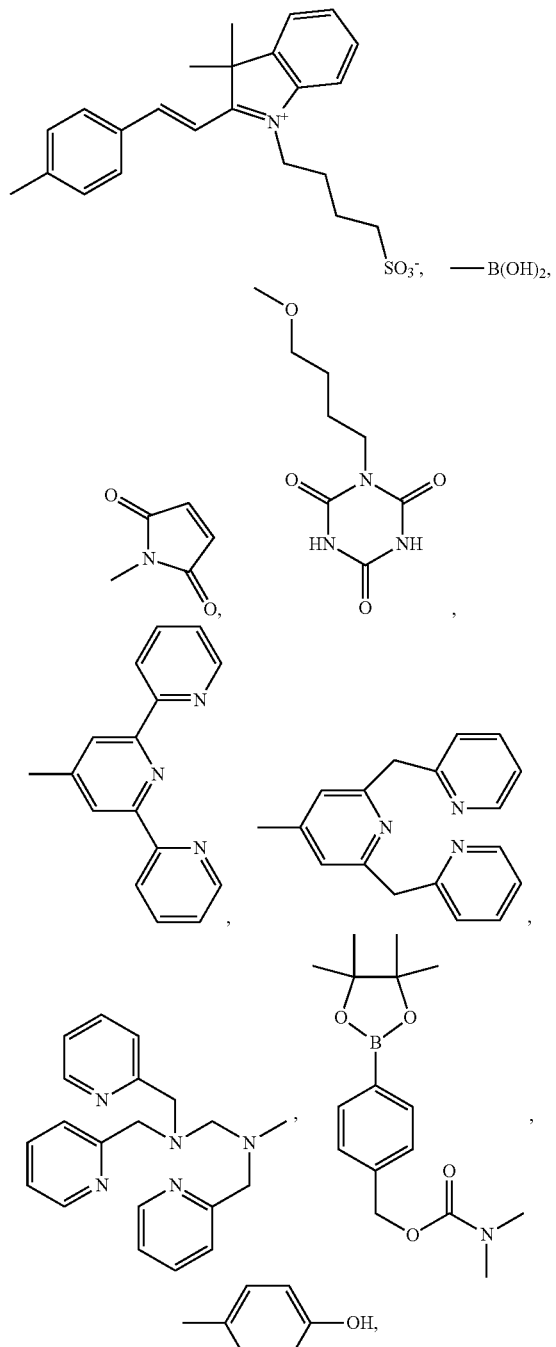

and at least one of R, R', R" or R'" is

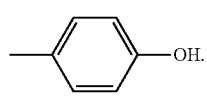

In an embodiment of the present invention, The formula I' to formula IX' can be prepared from a reaction between a formula I" to formula IX" and

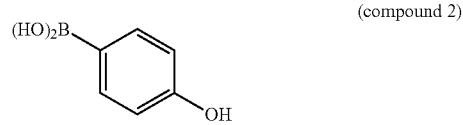

(preferably, via Suzuki coupling, Pd(PPh$_3$)$_4$, NaCO$_3$, THF-H$_2$O, reflux overnight), wherein the formula I" to formula IX" are selected from the group consisting of:

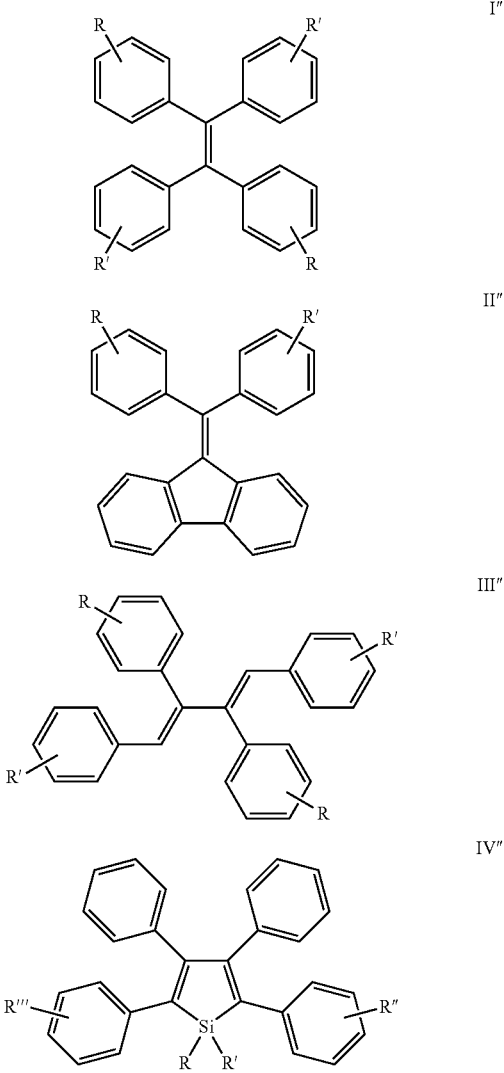

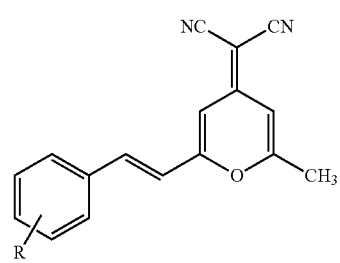

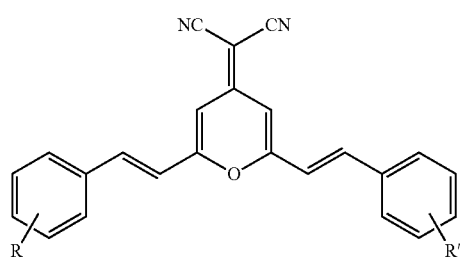
VI″
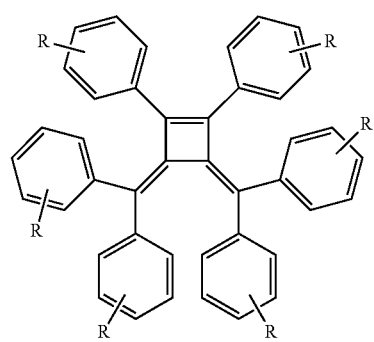
VII″
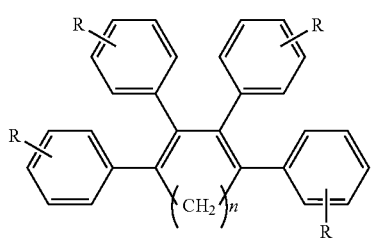
VIII″
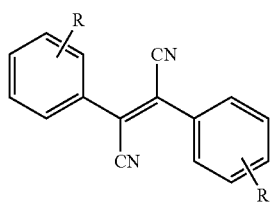
IX″
wherein
R, R', R″ or R‴ are selected from: H,
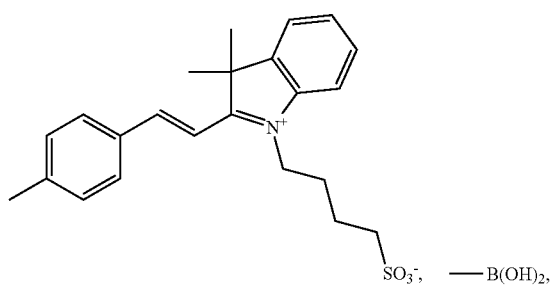
SO$_3^-$, —B(OH)$_2$,
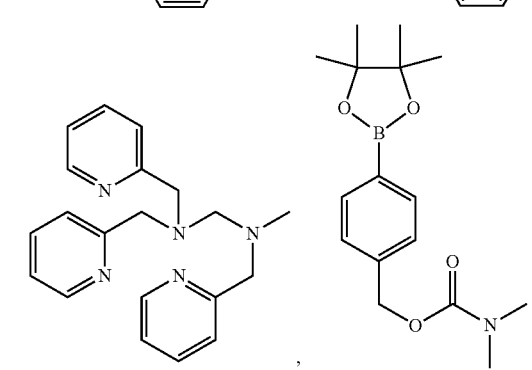
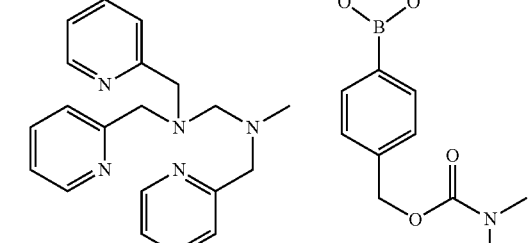
Br, and at least one of R, R', R″ or R‴ is Br.
In the present invention, a process for preparing the compound TPE-C comprises the reaction compound TPE-P with 2-nitrobenzyl bromide (3) (preferred to in the presence of Cs$_2$CO$_3$, MeCN, 80° C., 8 h).
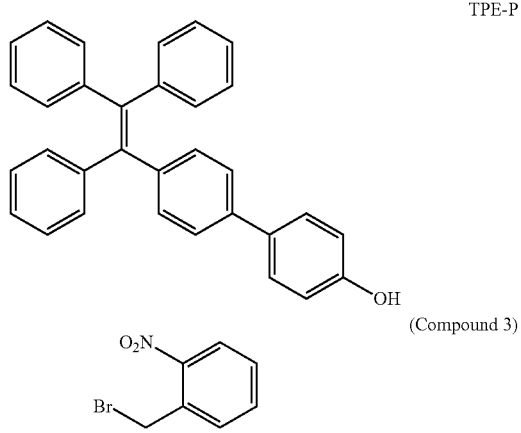
TPE-P
(Compound 3)

According to the present invention, the compound TPE-P can be prepared by the reaction between 4-bromotetraphenylethene (compound 1, TPE-Br) and (4-hydroxyphenyl) boronic acid (compound 2).

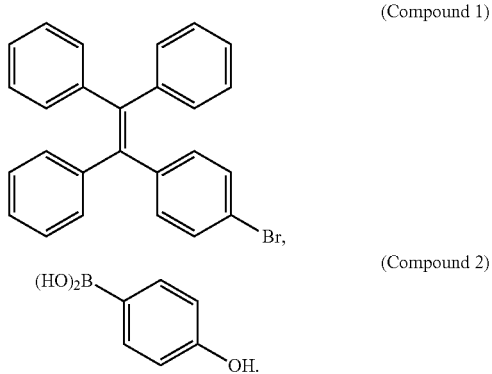

(Compound 1)

(Compound 2)

In an embodiment, TPE-P is synthesized via Suzuki coupling between 4-bromotetraphenylethene (1) and (4-hydroxyphenyl) boronic acid (2).

In the embodiment of the present invention, compound TPE-C is prepared by the following steps:

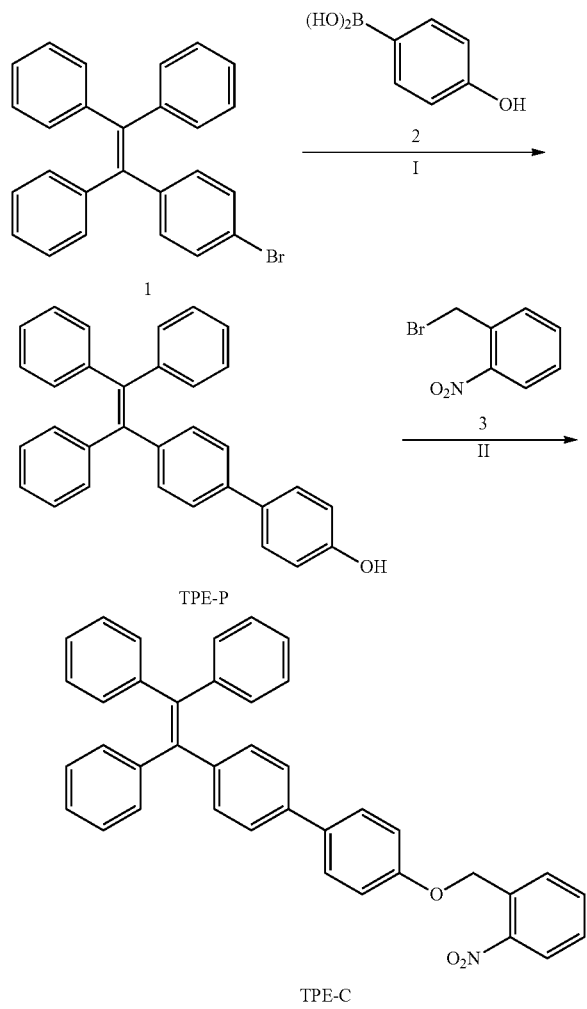

(1) TPE-P is synthesized via Suzuki coupling between 4-bromotetraphenylethene (1) and (4-hydroxyphenyl) boronic acid (2);

(2) The resultant TPE-P is then reacted with 2-nitrobenzyl bromide (3) in the presence of $Cs_2CO_3$ to furnish TPE-C.

The present invention is directed to a photoactivation process of the compound of any of the compound of the present invention.

According to the photoactivation process of the present invention, wherein the condition is in aggregated or solid state.

The present invention is directed to a method of applications of the caged compounds in photo-patterning and erasing.

According to the method of the present invention, wherein the compound is soaked with filter papers.

According to the method of the present invention, wherein photo-patterning are patterned by projector films' masks.

BRIEF DESCRIPTION OF DRAWINGS

Various embodiments will be described in detail with reference to the accompanying drawing.

DETAILS DESCRIPTION OF THE INVENTION

The present invention can be illustrated in further detail by the following examples. However, it should be noted that the scope of the present invention is not limited to the examples. They shoud be considered as merely being illustrative and representative for the present invention.

Figure 1:
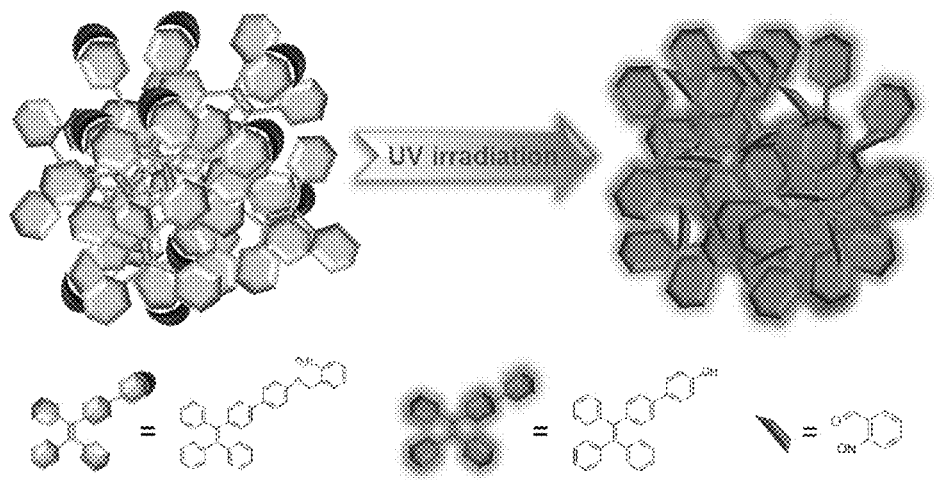
FIG. 1 Uncaging process of TPE-C.
Figure 2:
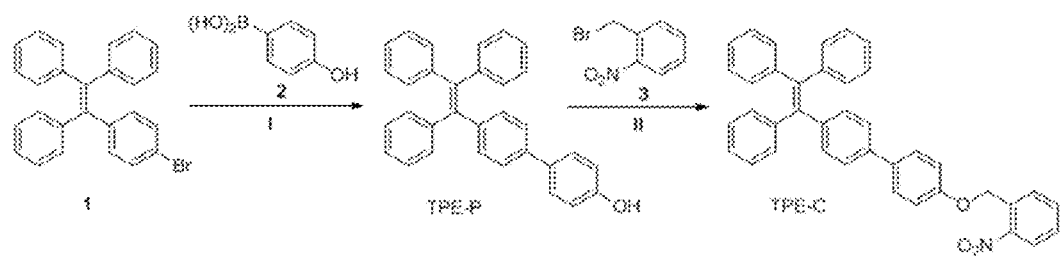
FIG. 2 Synthetic route to TPE-P and TPE-C.
Figure 3:
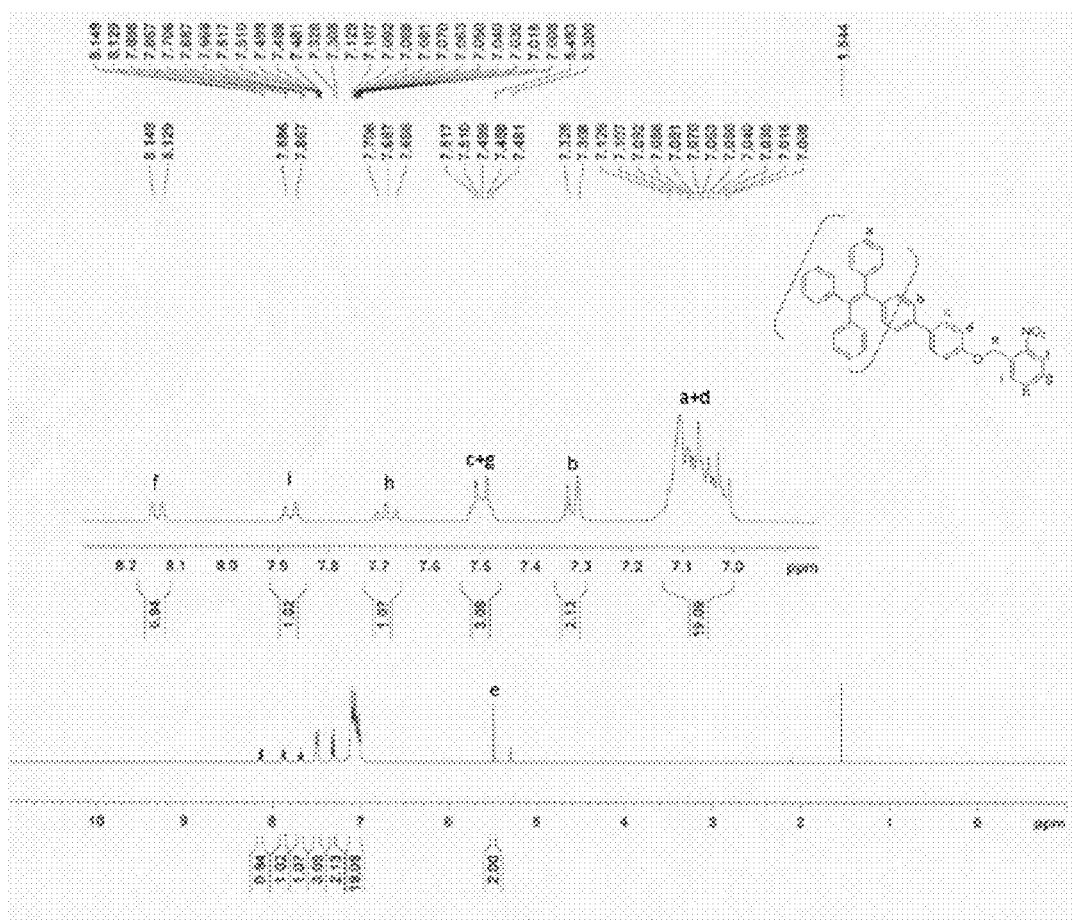
FIG. 3 $^1$H NMR spectrum of TPE-C in $CD_2Cl_2$.
Figure 4:
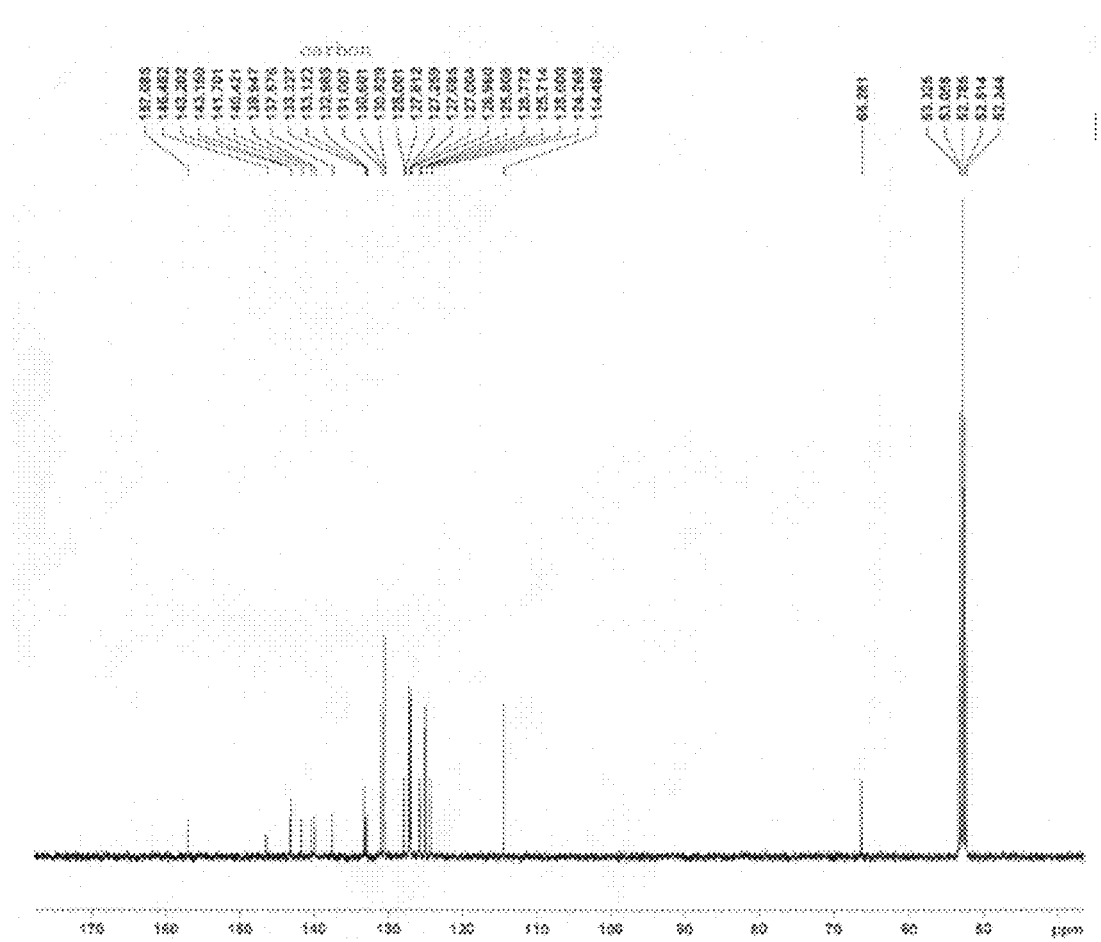
FIG. 4 $^{13}$C NMR spectrum of TPE-C in $CD_2Cl_2$.
Figure 5:
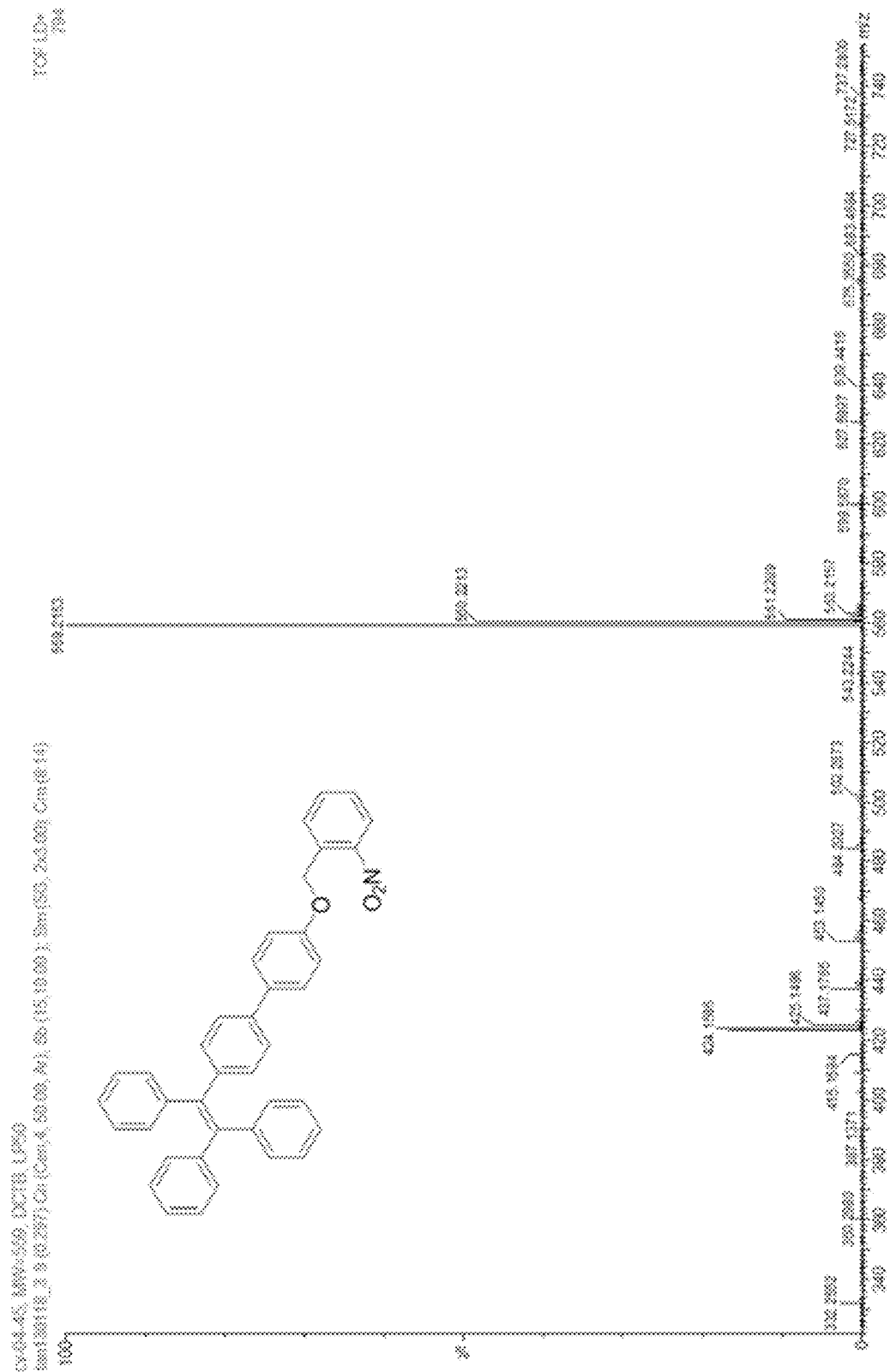
FIG. 5 High resolution mass spectrum (MALDI-TOF) of TPE-C.

The synthetic route of TPE-C is depicted in FIG. 2. TPE-P is synthesized via Suzuki coupling between 4-bromotetraphenylethene (1) and (4-hydroxyphenyl) boronic acid (2). The resultant TPE-P is then reacted with 2-nitrobenzyl bromide (3) in the presence of $Cs_2CO_3$ to furnish TPE-C. The product was characterized by NMR and mass spectroscopy and both of them gave satisfactory analysis data corresponding to their molecular structure (FIG. 3-5).

Figure 6:
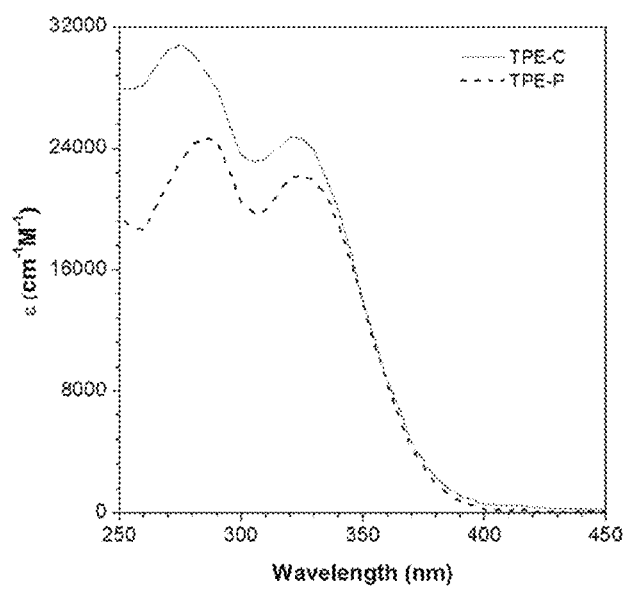
FIG. 6 Absorption spectra of TPE-P and TPE-C in THF solution. Concentration: 10 μM.
Figure 7:
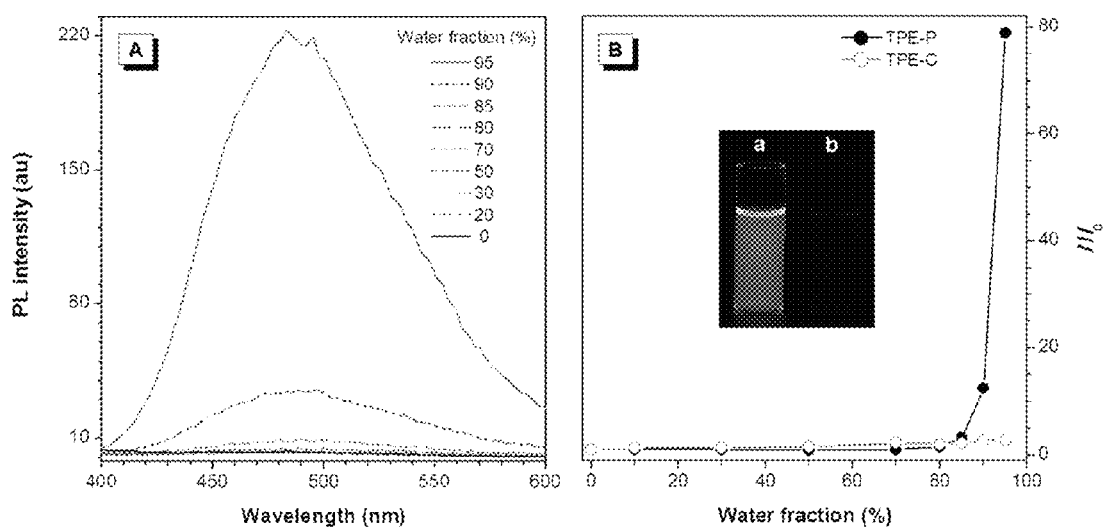
FIG. 7(A) PL spectra of TPE-P in THF/water mixture with different water fractions ($f_w$). (B) Plot of relative PL intensities ($I/I_0$) versus $f_w$. $I_0$ are the PL intensities at 488 nm of the dyes in THF solutions; Dye concentration: 10 μM; excitation wavelength: 320 nm. Inset: photographs of (a) TPE-P and (b) TPE-C in $f_w$=95% excited by hand-held UV lamp at 365 nm.
Figure 8:
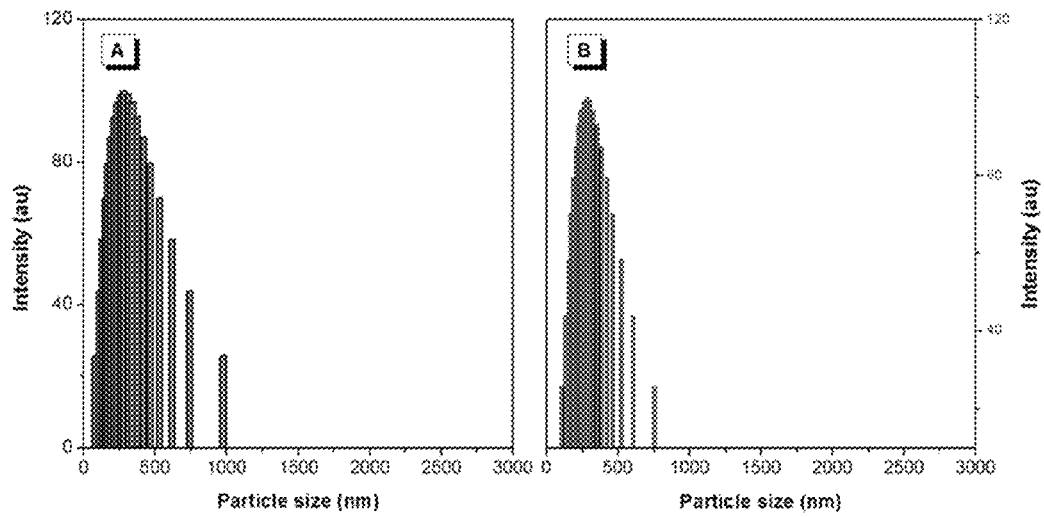
FIG. 8 Particle size analysis of TPE-P (A) and TPE-C (B) in the mixture of THF/water with $f_w$=95 vol %.
Figure 9:
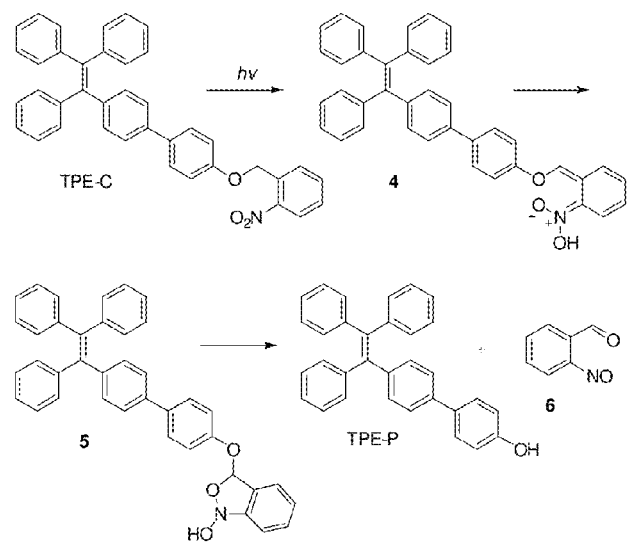
FIG. 9 Proposed uncaging mechanism of TPE-C.
Figure 10:
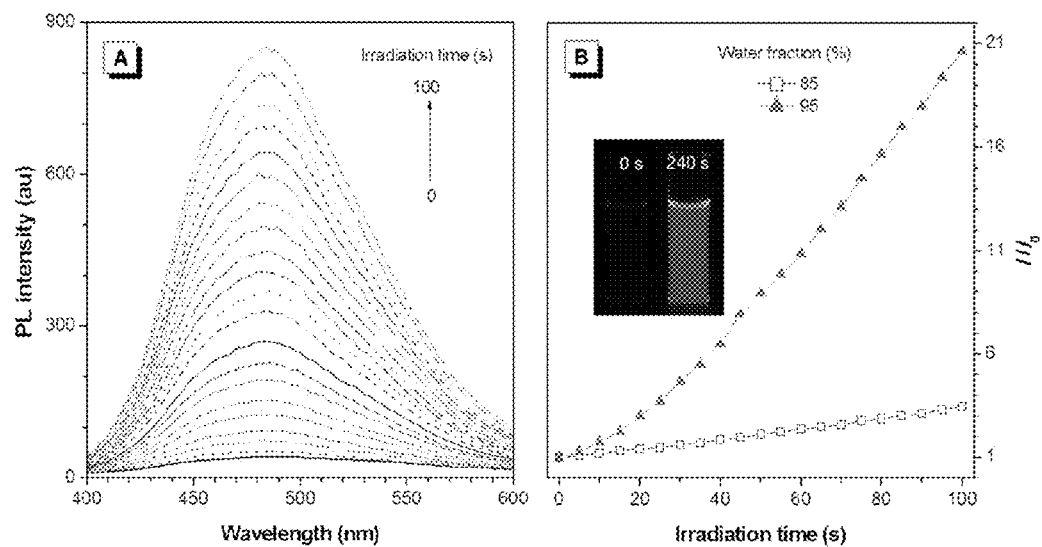
FIG. 10(A) PL spectra of TPE-C in 95% $f_w$ with different irradiation time. (B) Change in PL intensities at 488 nm of TPE-C in different $f_w$ versus irradiation time. Concentration: 10 μM; excitation wavelength: 320 nm. Inset: photographs of TPE-C in 95% $f_w$ excited by hand-held UV lamp at 365 nm under UV irradiation for 0 s and 240 s.
Figure 11:
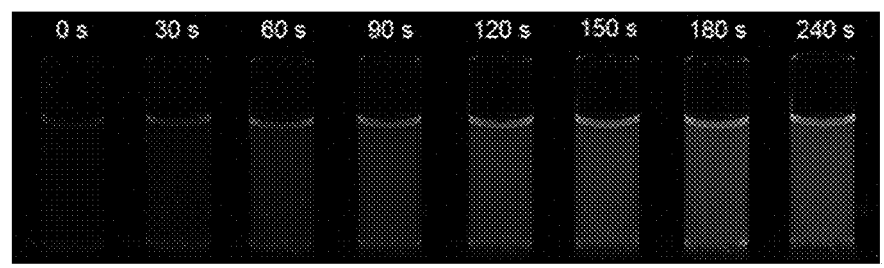
FIG. 11 Fluorescent photographs of TPE-C in the mixture of THF/water with $f_w$=95 vol % taken at different irradiation time.

The UV spectra of both TPE-C and TPE-P in THF solution exhibit an absorption maximum at 320 nm (FIG. 6). As shown in FIG. 7, both TPE-C and TPE-P are non-fluorescent in pure THF solution. The emission of TPE-P increases swiftly when the water fraction ($f_w$) in the mixture of THF/water exceed 85%. When $f_w$=95%, the PL intensity at 488 nm is 80-fold higher than that in pure THF solution. The fluorescent enhancement of TPE-P is attributed to the formation of nanoaggregates (FIG. 8), suggesting that TPE-P is AIE-active. On the other hand, TPE-C remains non-emissive although the nanoaggregates have formed when 95% of water is added to the THF solution. The PL results indicated that the emission of TPE-C in aggregated state is quenched by 2-nitrobenzene through PeT process. Inspired by the uncaging process in conventional systems, TPE-C is expected to respond to UV irradiation. As the proposed uncaging mechanism shown in FIG. 9, the 2-nitrobenzyl group in TPE-C is cleaved by UV irradiation and TPE-P and 2-nitrosobenzaldehyde are readily formed. Since TPE-P is highly emissive in aggregated state, we utilized PL measurements to monitor the uncaging process of TPE-C in aggregated state. As shown in FIG. 10, TPE-C shows a weak emission in both the mixtures of THF/water with $f_w$=85% and 95%. Their PL peak intensities at 488 nm are gradually enhanced along with the UV irradiation time, indicating that the TPE-P is formed during UV treatment (FIG. 10A). The PL enhancement in $f_w$=95% is faster than of $f_w$=85%, it should be because the TPE-P aggregates in 95% water content are more compressed and the intramolecular motions are more restricted (FIG. 10B). The fluorescent photos of TPE-C in the mixture of THF/water with $f_w$=95% taken under UV illumination also demonstrate such an uncaging process (FIG. 11).

Figure 12:
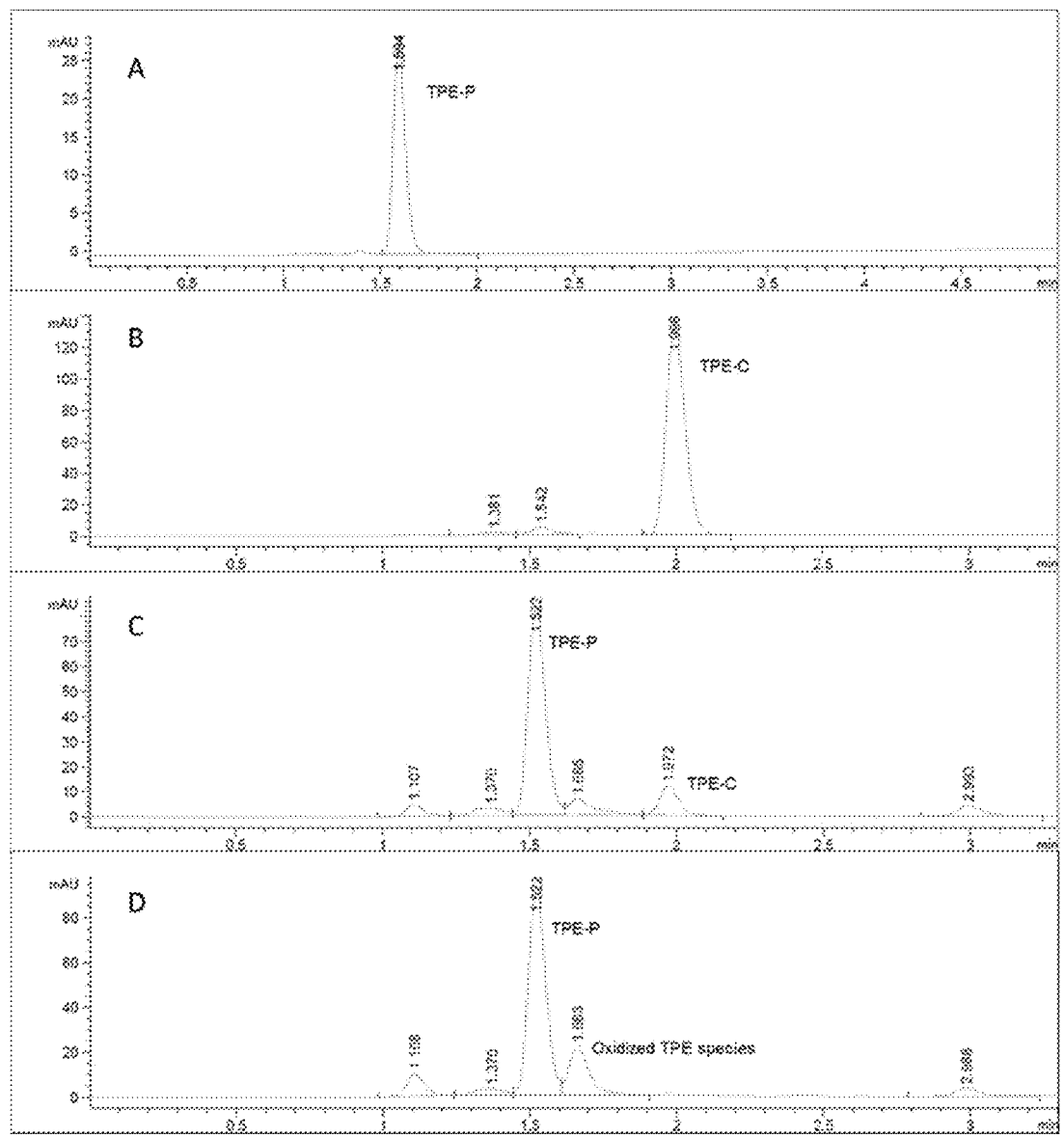
FIG. 12 HPLC spectra of TPE-P (A) and TPE-C before (B), and after being irradiated under UV light for 3 (C) and 8 (D) min respectively. All samples were eluted with acetonitrile at a flow rate of 1 mL/min.
Figure 13:
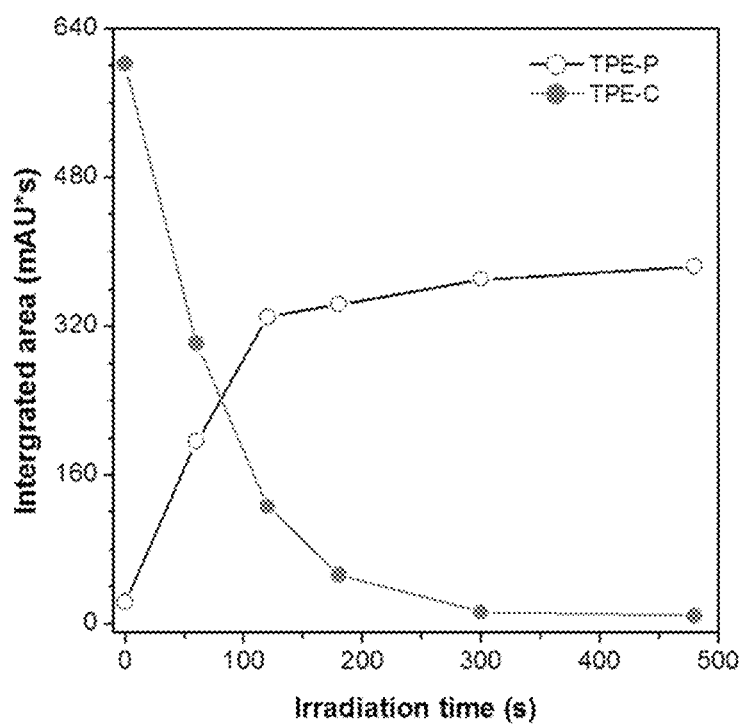
FIG. 13 Change in the integrated area of the specific peaks in HPLC spectra versus irradiation time.
Figure 14:
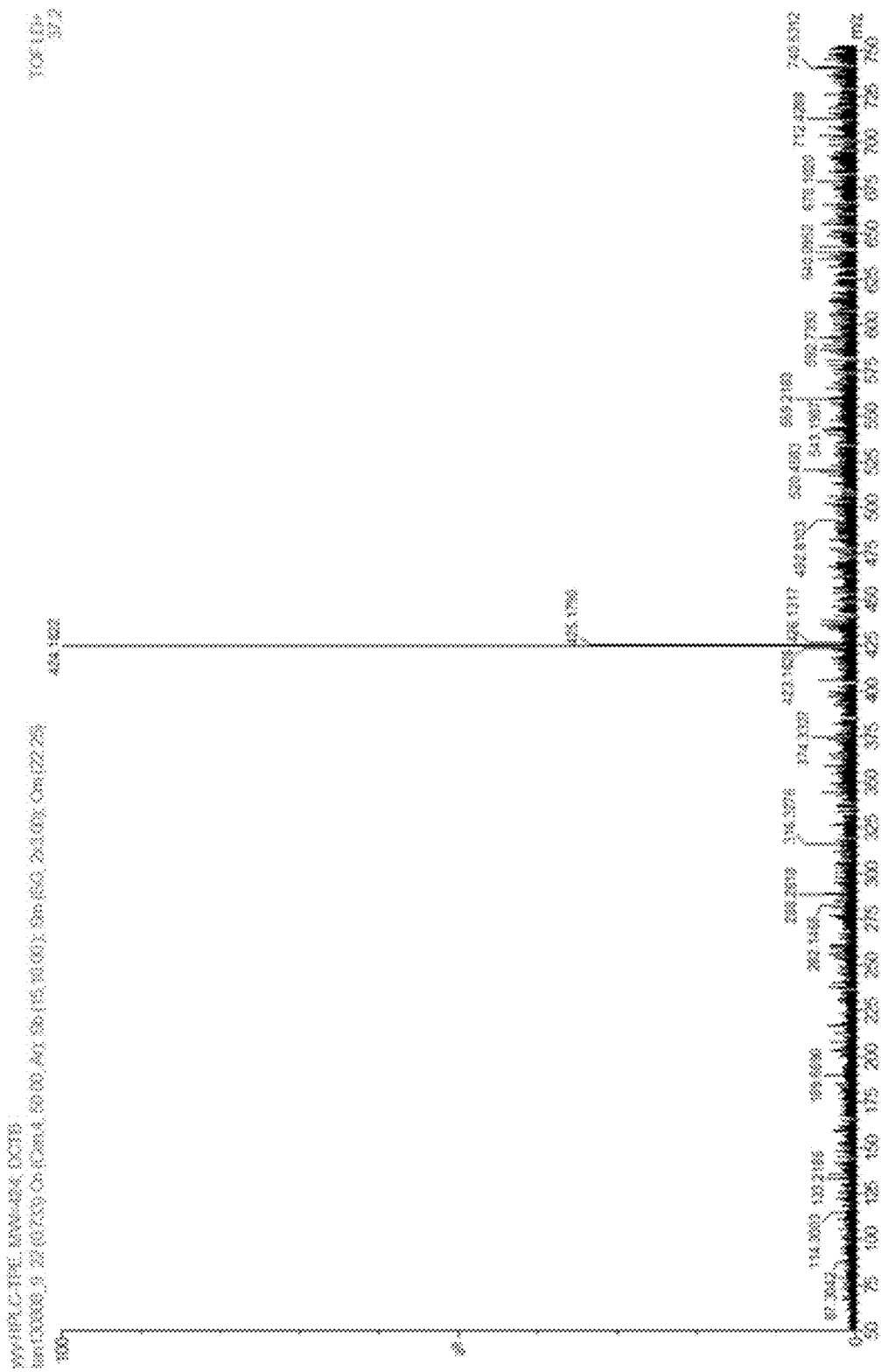
FIG. 14 High resolution mass spectrum (MALDI-TOF) of the peak at 1.5 min in HPLC spectrum.

To further verify whether the cyan fluorescence is attributed to the formation of TPE-P, we conducted high-performance liquid chromatography (HPLC) to monitor the uncaging process. We first run the pure TPE-P and TPE-C using acetonitrile as the references. The peaks for TPE-P and TPE-C are observed at 1.5 and 2.0 min, respectively (FIG. 12). The TPE-C aggregates in the mixture of THF/water with $f_w$=95% are then irradiated by UV light and the samples are taken out for HPLC analysis in every minute. The HPLC spectra show that the peak area for TPE-C is decreasing while the peak area for TPE-P is increasing along with the UV irradiation time (FIG. 13), which is consistent with the PL results. As indicated by the mass analysis, the isolated product from HPLC at 1.5 min has an exact mass of 424.1822 (FIG. 14), which corresponds to the mass of TPE-P.

Synthesis of TPE-P.

Into a 250 mL two-necked round bottom flask equipped a condenser. 4-Bromotetraphenylethlene (2.00 g, 4.86 mmol), (4-hydroxylphenyl)boronic acid (2, 0.74 g, 5.35 mmol), sodium bicarbonate (5.14 g, 48.62 mmol) and $Pd(PPh_3)_4$ (0.17 g, 0.15 mmol) were dissolved in to 90 mL distilled THF and 30 mL water under nitrogen. The mixture was heated to reflux overnight. After being cooled to room temperature, the mixture was extracted with dichloromethane for three times. The organic phase was combined and washed with water and dried over anhydrous sodium sulfate. After the evaporation of solvents, the crude product was purified by silica gel column chromatography using DCM/hexane in the volume ratio of 1:3 as eluent. The white solid was obtained in the yield of 78%. $^1$H NMR (400 MHz, $CDCl_3$): 7.42 (dd, 2H, J=8.8 Hz), 7.28 (dd, 2H, J=6.8 Hz), 7.13-7.02 (m, 17H), 6.84 (dd, 2H, J=8.8 Hz). $^{13}$C NMR (100 MHz, $CDCl_3$): 154.3, 143.2, 141.5, 140.3, 139.9, 137.7, 132.8, 131.1, 130.8, 130.7, 127.5, 127.1, 127.1, 127.0, 125.8, 125.8, 125.1. $^1$H NMR (400 MHz, $CD_2Cl_2$): 7.46 (dd, 2H, J=8.8 Hz), 7.33 (dd, 2H, J=8.4 Hz), 7.16-7.05 (m, 17H), 6.88 (dd, 2H, J=8.4 Hz). $^{13}$C NMR (100 MHz, $CD_2Cl_2$): 154.7, 143.2, 141.5, 140.4, 140.0, 137.7, 132.4, 131.0, 130.6, 130.5, 127.3, 127.1, 127.0, 125.8, 125.7, 124.9. HRMS (MALDI-TOF) m/z 424.1821 (Mt, calcd. 424.5324).

Synthesis of TPE-C.

Into a two-necked round bottom flask, TPE-P (0.20 g, 0.47 mmol), 2-nitrobenzyl bromide (3, 0.12 g, 0.57 mmol) and cesium carbonate (0.18 g, 0.57 mmol) were dissolved in 7 mL acetonitrile under nitrogen atmosphere. The mixture was heated at 70° C. overnight. After being cooled to room temperature, the mixture was extracted with dichloromethane for three times. The organic phase was combined and washed with water and dried over anhydrous sodium sulfate $Na_2SO_4$. After the evaporation of solvents, the crude product was purified by silica gel column chromatography using DCM/hexane in the volume ratio of 1:4 as eluent. The pale yellow solid was obtained in the yield of 70%. 1H NMR (400 MHz, $CD_2Cl_2$): 8.14 (dd, 1H, J=8.0 Hz), 7.88 (dd, 1H, J=7.6 Hz), 7.69 (t, 1H, J=7.6 Hz), 7.15-7.48 (m, 3H), 7.32 (dd, 2H, J=8.0 Hz), 7.13-7.01 (m, 19H), 5.49 (s, 2H). 13C NMR (100 MHz, $CD_2Cl_2$): 157.1, 146.5, 143.2, 141.7, 140.4, 137.6, 133.3, 133.1, 131.0, 130.6, 130.5, 128.0, 127.8, 127.3, 127.09, 127.0, 125.8, 125.7, 125.0, 124.3, 114.5. HRMS (MALDI-TOF) ink 559.2153 (Mt, calcd. 559.6925).

Application of TPE-C

Figure 15:
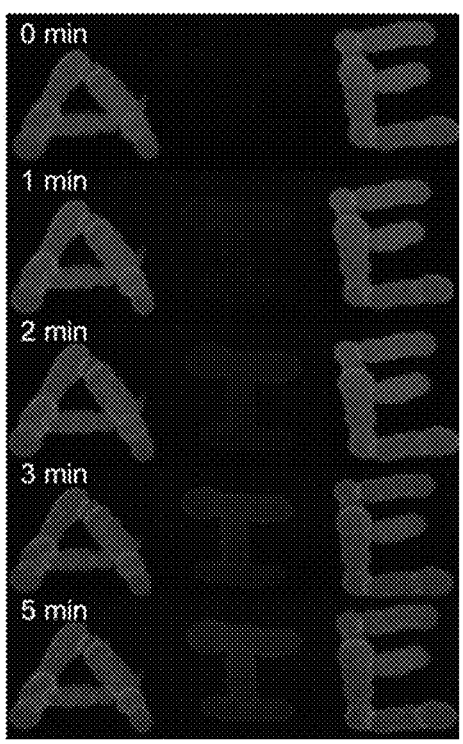
FIG. 15 Photographs of filter paper at ambient conditions taken under UV irradiation at 365 nm with different irradiation time. Letters "A" and "E" were written by TPE-P and letter "I" was written by TPE-C using capillary tubes.

Inspired by rapid and highly efficient release of TPE-P from the caged compound TPE-C in aggregated state, we explored the possibility to utilize TPE-C as a kind of UV activatable fluorescent material for photo-patterning and anti-counterfeiting related applications. First of all, we tried to use filter paper as a substrate for writing. As shown in FIG. 15, the letter "I" is written with TPE-C while the letters "A" and "E" are written with TPE-P for comparison. Before UV treatment, the letters "A" and "E" are highly emissive but the letter "I" is still non-fluorescent. As the increase of UV irradiation time, the emission of letter "I" becomes stronger. Although the emission of letter "I" is still weaker than the letters "A" and "E", it is understandable that the photoactivation process may only occur on the surface of filter paper and most of the TPE-C has not been uncaged.

In addition to the fluorescent writing, TPE-C possesses the potential to be used in anti-counterfeiting applications.

Figure 16:
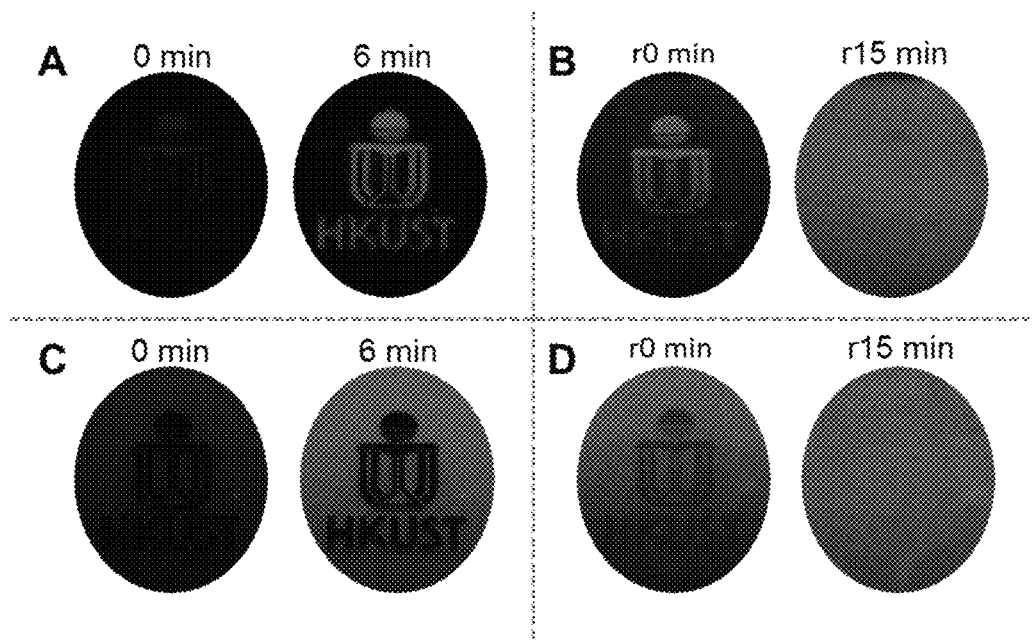
FIG. 16 Photographs of the process of (A and C) photo-pattern by a mask with HKUST logo under UV irradiation and (B and D) pattern erasing process after removing the mask under further UV irradiation.
Figure 17:
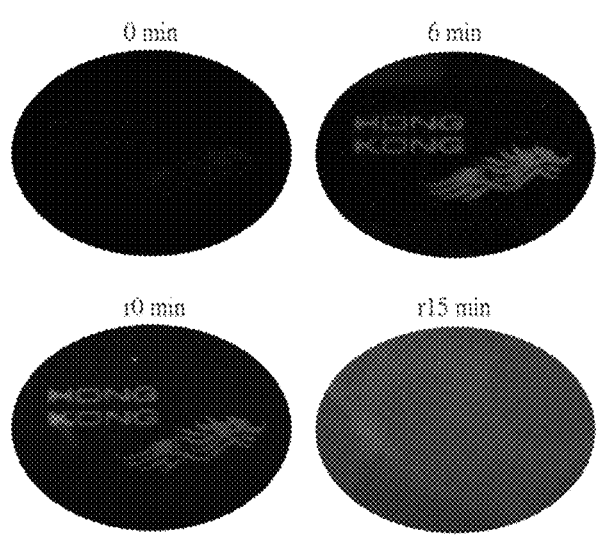
FIG. 17 Photographs of the process of photo-pattern by a mask with HKSAR logo under UV irradiation and pattern erasing process after removing the mask under further UV irradiation.

Since we have demonstrated that the photo-activation can be carried out on the filter paper, we can conveniently fabricate patterns or erase patterns by adding or removing a mask. Filter papers are firstly soaked with the THF solution of TPE-C and dried by compressed air. Two projector films with HKUST logo, one is transparent image (FIG. 16A) while the other one is dark image (FIG. 16C), were covered onto the filter papers. The HKUST logo gradually emerged on the filter papers upon UV irradiation. For the film with transparent logo, the frame structure displays brighter emission than the surrounding. On the contrary, the frame structure shows dimmer emission than the surrounding when a mask with a dark logo is used. Moreover, the patterns can be erased by further UV irradiation after removing the masks (FIGS. 16B and 16D). Since the caged fluorophore in both logo and surrounding areas are activated, the whole filter papers are emissive and the patterns cannot be seen as a resulted. To demonstrate the flexibility of this method, we used other films with different logo to perform the same experiment (FIG. 17). All the frame structures of patterns can be presented and also be erased. These photo-patterning and pattern erasing techniques can be potentially applied for one-time anti-counterfeiting protection, especially for high-valued products. We have designed and synthesized a new caged fluorophore based on a TPE derivative and a 2-nitrobenzyl group. The caged compound can be photoactivated and induced to emit strong cyan fluorescence in the aggregated state or solid state by UV irradiation. This property of the caged fluorophore enables it to be applied in photo-patterning and anti-counterfeiting related applications.

We claim:

1. A caged compound, comprising an AIE compound as a luminophore and a 2-nitrobenzyl group as a quencher, wherein the 2-nitrobenzyl group is

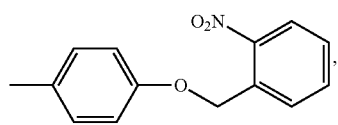

wherein the caged compound is selected from the group consisting of

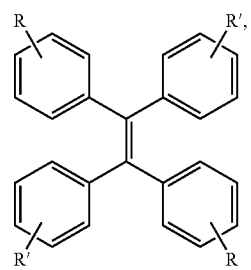
I

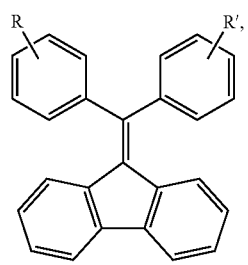
II

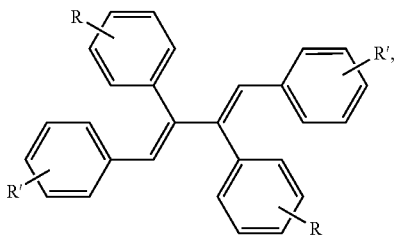
III

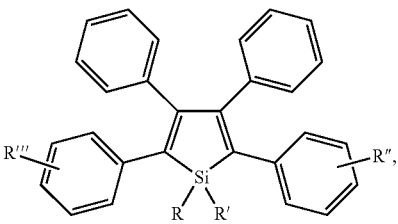
IV

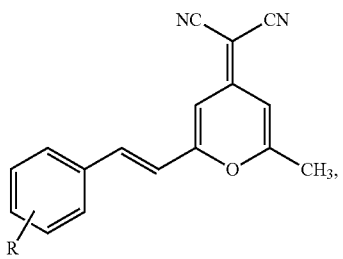
V

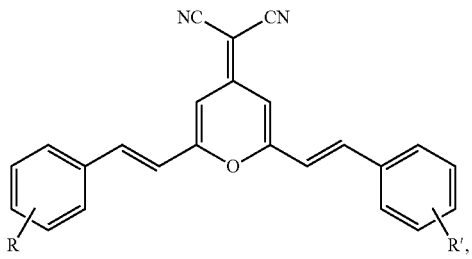
VI

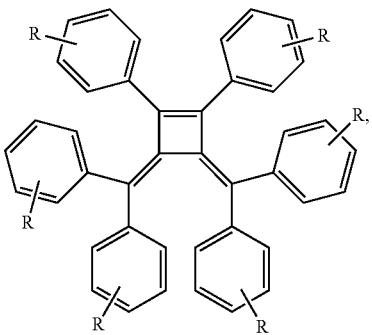
VII

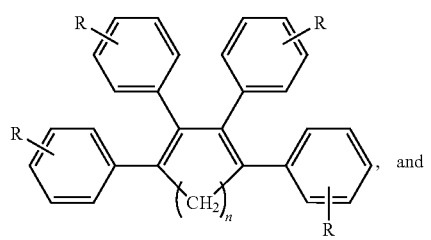
, and VIII

-continued

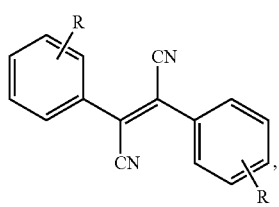
IX wherein R, R', R" or R'" are independently selected from the group consisting of H,

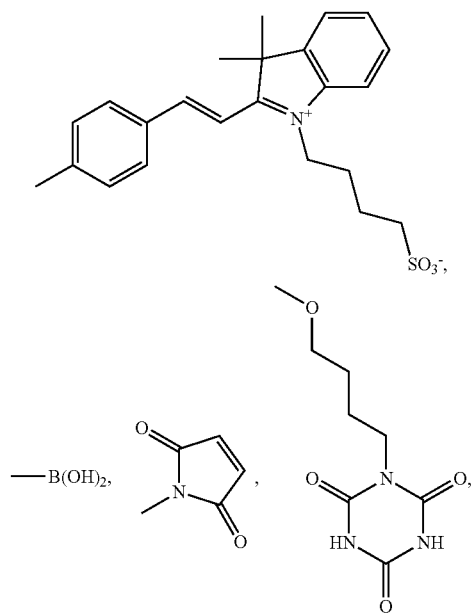

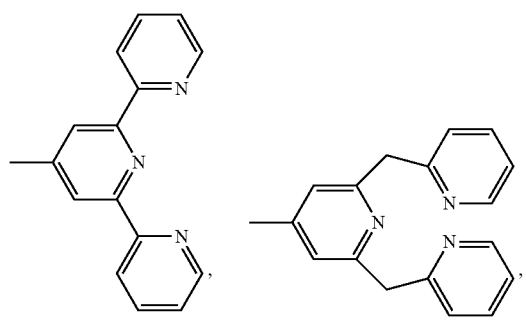

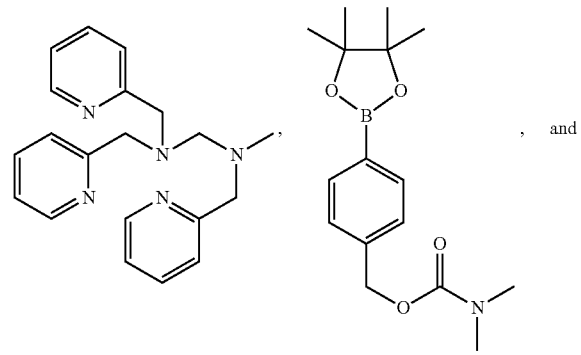

-continued

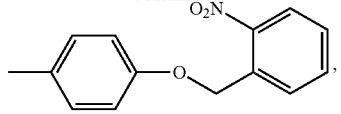 [SMILES: Cc1ccc(OCc2ccccc2[N+](=O)[O-])cc1]

with the proviso that the caged compound comprises at least one

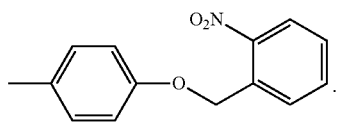

2. The caged compound of claim 1, wherein the caged compound is TPE-C

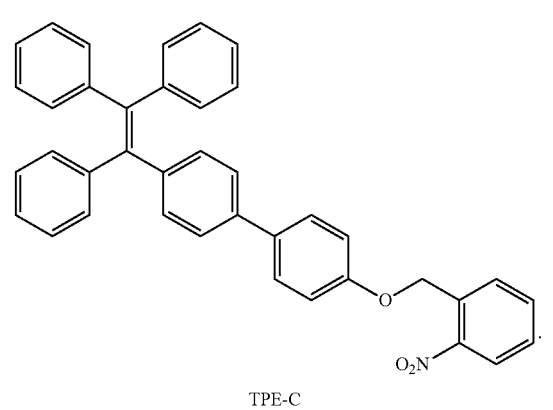 [SMILES: O=[N+]([O-])c1ccccc1COc1ccc(-c2ccc(C(=C(c3ccccc3)c3ccccc3)c3ccccc3)cc2)cc1]

TPE-C

3. A process for preparing a caged compound of claim 1, wherein the process comprises reacting a compound selected from the group consisting of compounds of formula I', formula II', formula III', formula IV', formula V', formula VI', formula VII', formula VIII', and formula IX' with 2-nitrobenzyl bromide

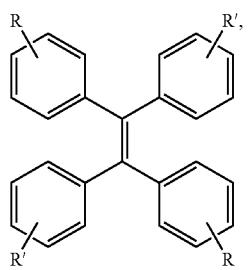
I'

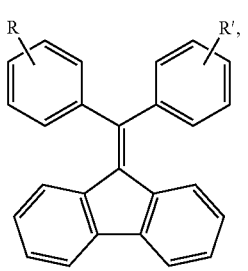
II'

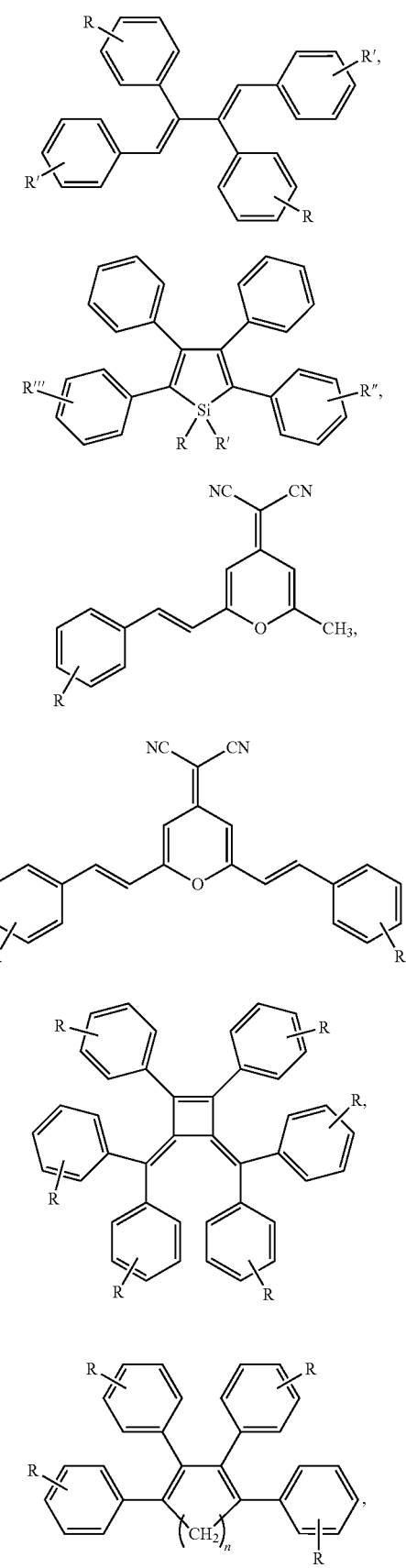
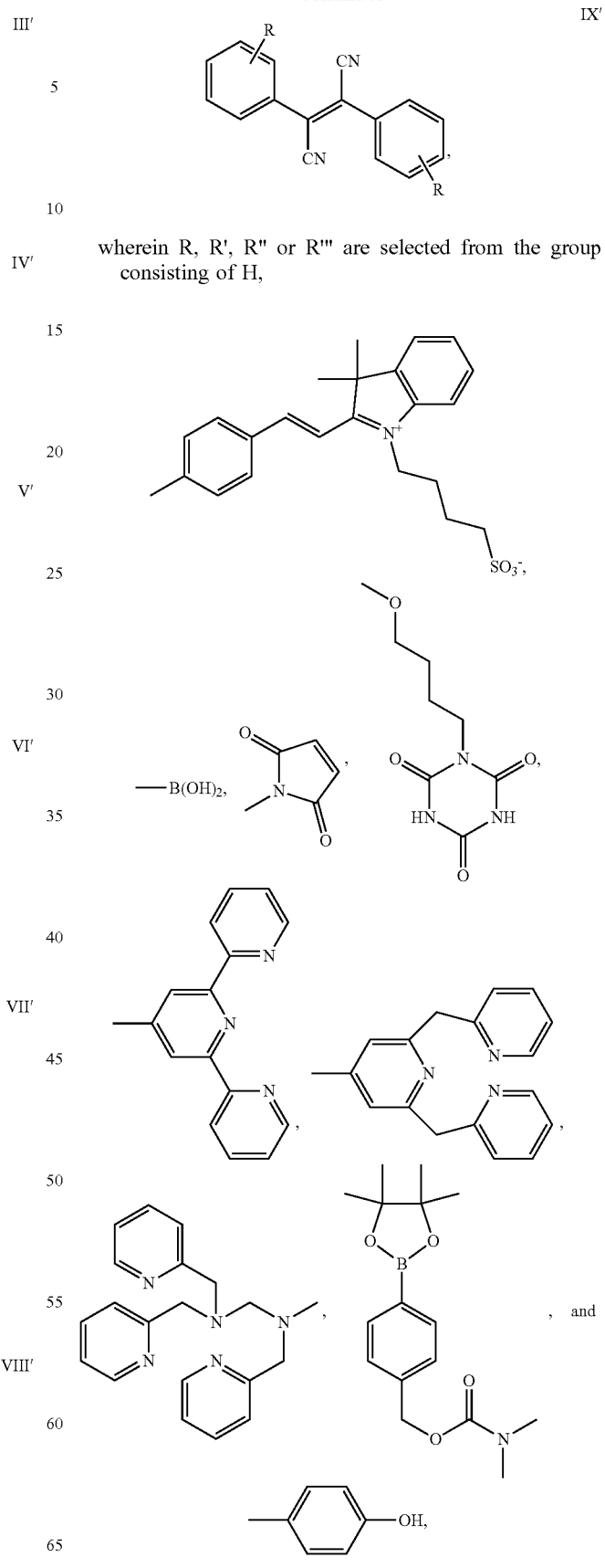
wherein R, R', R" or R'" are selected from the group consisting of H, and at least one of R, R', R" or R'" is

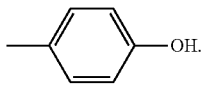

4. The process of claim 3, comprising reacting TPE-P with 2-nitrobenzyl bromide (compound 3) to form TPE-C

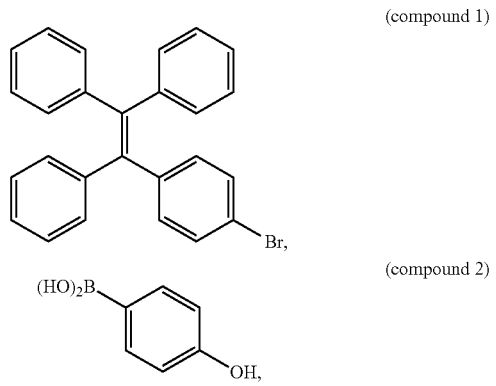

TPE-P (compound 3)

5. The process of claim 4, wherein the compound TPE-P is prepared by reacting 4-bromotetraphenylethene (compound 1, TPE-Br) with (4-hydroxyphenyl) boronic acid (compound 2), (compound 1)

(compound 2)

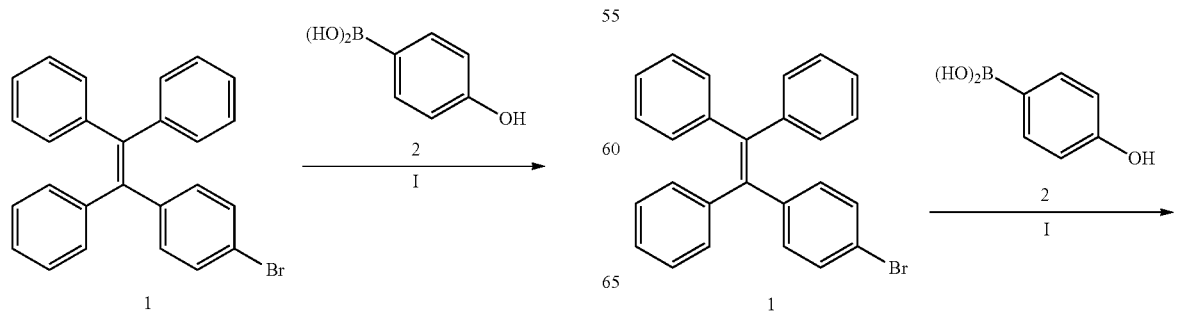

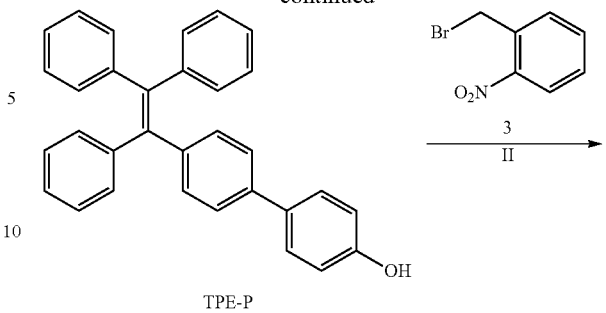

TPE-P

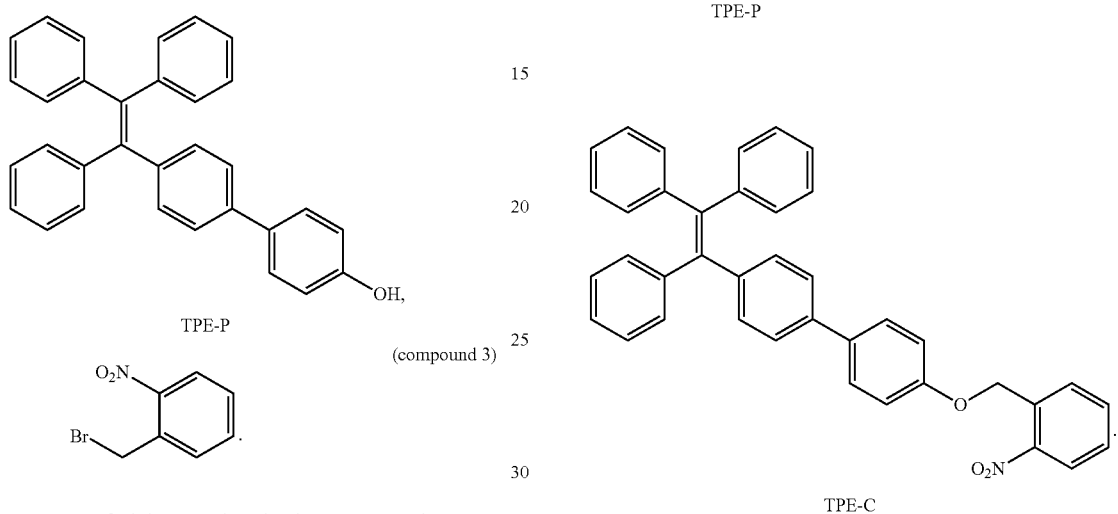

TPE-C

6. A photoactivation process of a caged compound of claim 1, comprising exposing the caged compound of claim 1 to lights.

7. The photoactivation process of claim 6, wherein the caged compound of claim 1 is in an aggregated or solid state.

8. A method of photo-patterning, comprising:
loading a caged compound of claim 1 on a substrate;
placing a mask over the substrate to form a masked substrate, wherein a portion of the mask is transparent to a UV light;
irradiating the masked substrate using the UV light so that the UV light passes through the portion of the mask transparent to the UV light and activates the caged compound of claim 1 underneath the mask, wherein the activated caged compound emits light to form a pattern on the substrate.

9. The process of claim 4, wherein the compound TPE-C is prepared by the following steps:

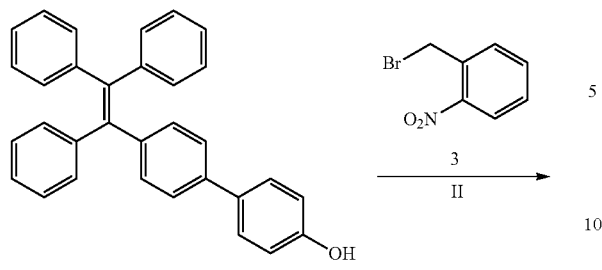

TPE-P

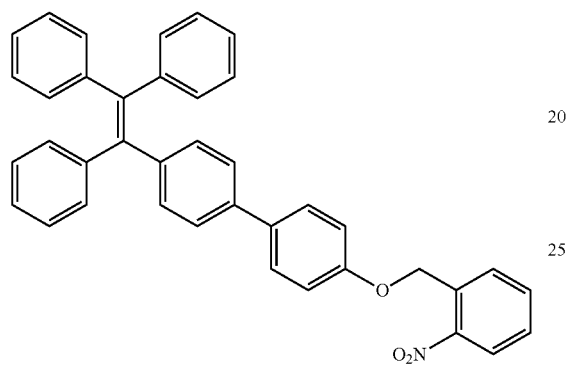

TPE-C wherein TPE-P is synthesized via Suzuki coupling between 4-bromotetraphenylethene (1) and (4-hydroxyphenyl) boronic acid (2), and the TPE-P further reacts with 2-nitrobenzyl bromide (3) in the presence of $Cs_2CO_3$ to obtain TPE-C.

10. The process of claim 3, wherein compounds of formula I', formula II', formula III', formula IV', formula V', formula VI', formula VII', formula VIII', and formula IX' respectively are prepared by reacting compounds of formula I", formula II", formula III", formula IV", formula V", formula VI", formula VII", formula VIII", and formula IX" with

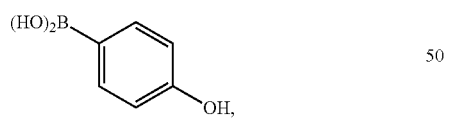

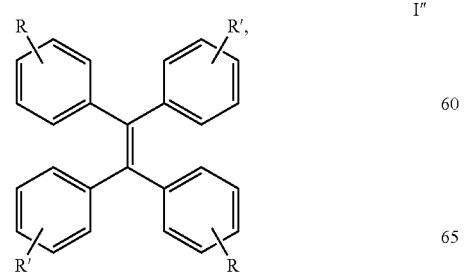

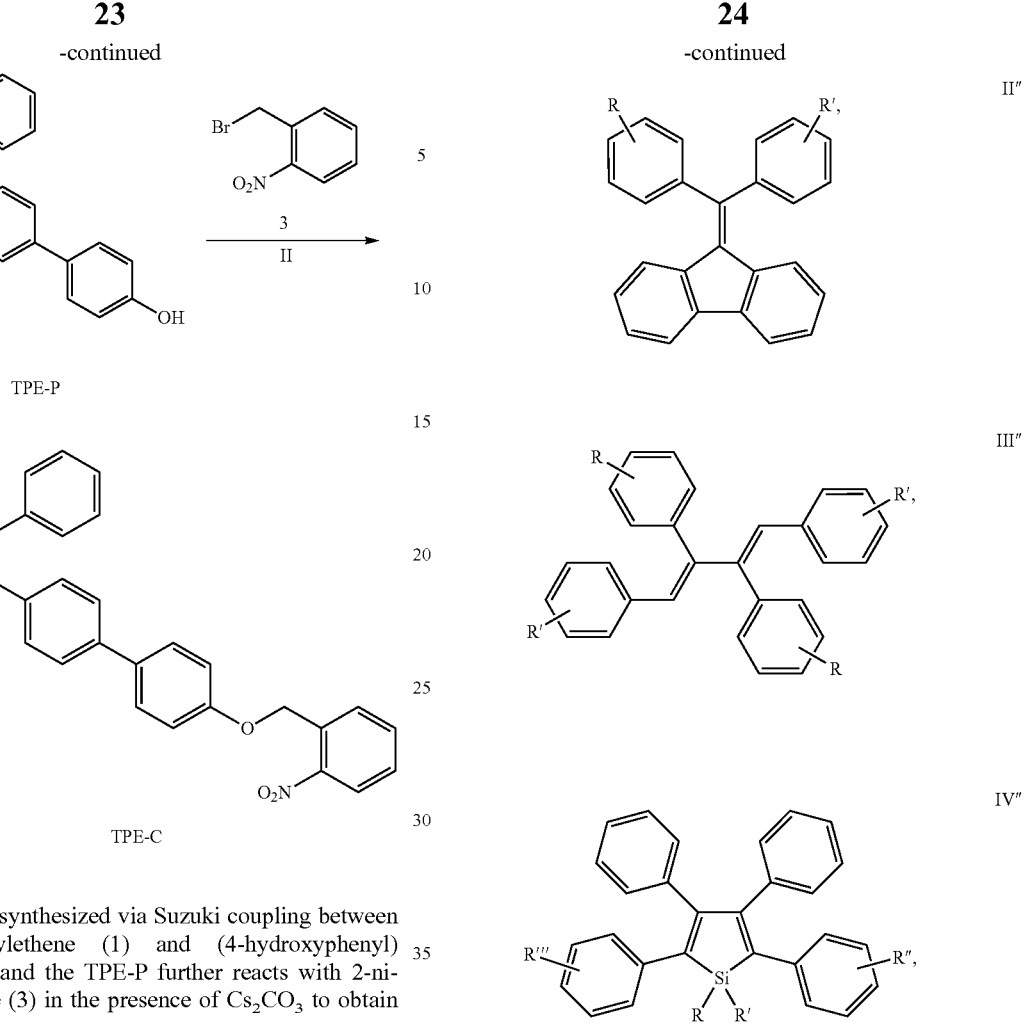

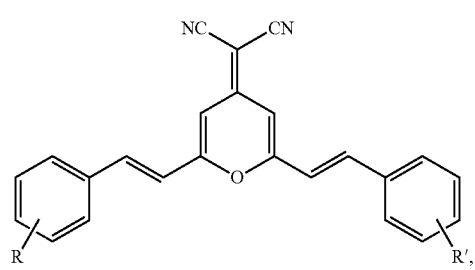

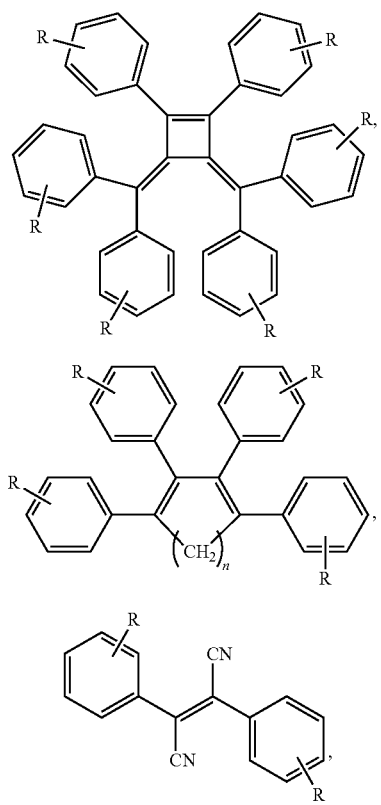
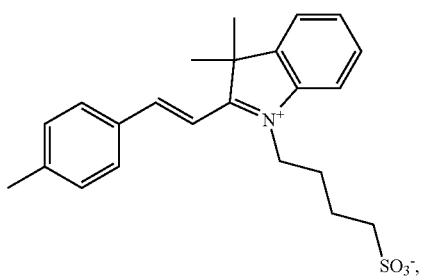
wherein R, R', R" or R'" are selected from the group consisting of H,
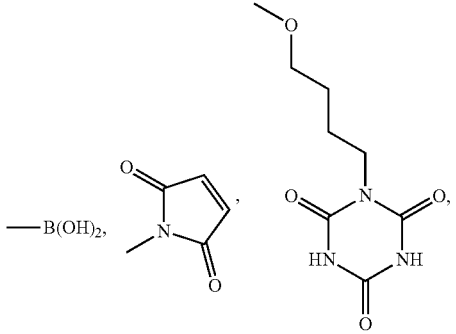
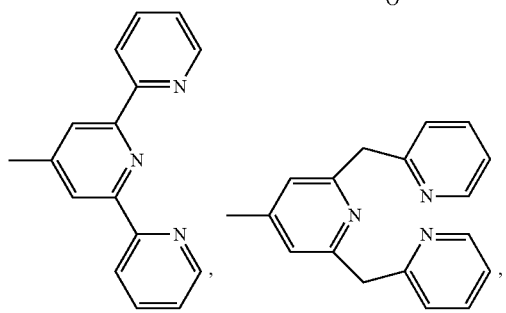
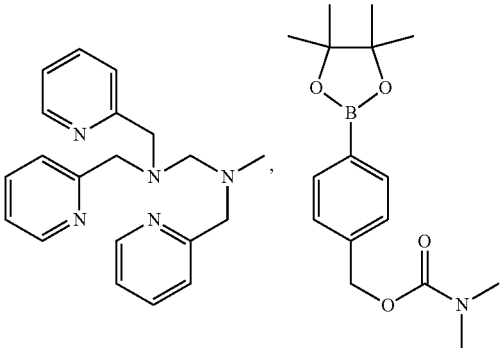
and Br,
and at least one of R, R', R" or R'" is Br.
11. The method of claim 8, further comprising:
removing the mask from the substrate; and
irradiating the substrate without the mask so that substantially all the caged compound of claim 1 on the substrate is activated.
* * * * *